United States Patent [19]
Kennedy

[11] Patent Number: 5,695,692
[45] Date of Patent: Dec. 9, 1997

[54] SELF-ROTATING AIR FRESHNER CARTRIDGE AND METHOD OF DISPENSING DIFFERENT AIR FRESHENING VAPORS

[75] Inventor: James Walter Kennedy, Buxted, United Kingdom

[73] Assignee: David Kennedy (Engineers) Holdings Limited, United Kingdom

[21] Appl. No.: 588,429

[22] Filed: Jan. 18, 1996

[30] Foreign Application Priority Data

Jan. 18, 1995 [GB] United Kingdom ............... 9501065

[51] Int. Cl.$^6$ ........................................... B01F 3/04
[52] U.S. Cl. ............................ 261/30; 261/DIG. 65; 239/60; 422/124
[58] Field of Search .................... 261/30, DIG. 65; 239/54, 57, 60; 422/124

[56] References Cited

U.S. PATENT DOCUMENTS

| | | | |
|---|---|---|---|
| 3,993,444 | 11/1976 | Brown | 261/DIG. 65 |
| 4,615,486 | 10/1986 | Konicek | 261/DIG. 65 |
| 5,023,020 | 6/1991 | Machida et al. | 261/DIG. 65 |
| 5,178,327 | 1/1993 | Palamand et al. | 239/60 |
| 5,180,107 | 1/1993 | Lindauer | 239/35 |
| 5,220,636 | 6/1993 | Chang | 392/392 |
| 5,259,062 | 11/1993 | Pelonis | 261/DIG. 65 |
| 5,565,148 | 10/1996 | Pendergrass, Jr. | 261/DIG. 65 |

FOREIGN PATENT DOCUMENTS

786269  11/1957  United Kingdom .

*Primary Examiner*—Tim R. Miles
*Attorney, Agent, or Firm*—Londa and Traub LLP

[57] ABSTRACT

Described is an air freshener unit comprising a container, a disc-shaped cartridge of air freshening material rotatably mounted about a horizontal axis within the container, and a discharge outlet in the wall of the container to allow the air freshening vapor to be dispensed. The container has baffle means adapted to allow a faster rate of evaporation of the air freshening material in one part of the cartridge relative to the remainder of the cartridge. The quicker rate of evaporation of the offset part causes the center of gravity to self-rotate within the container. The disc-shaped cartridge comprises a holder having a hub portion for rotatably mounting the cartridge in the container and holding means for supporting air freshening material in block form uniformly around the hub portion. The hub portion has oppositely directed stub shafts for location in apertures in opposed walls of the container, the apertures allowing the cartridge to rotate.

16 Claims, 6 Drawing Sheets

SELF-ROTATING AIR FRESHNER CARTRIDGE AND METHOD OF DISPENSING DIFFERENT AIR FRESHENING VAPORS

FIELD OF THE INVENTION

This invention relates to dispensing one or more air freshening vapours. The invention also relates to an air freshener unit, and a cartridge of air freshening material therefor.

BACKGROUND OF THE INVENTION

It is known to provide a container comprising a casing housing a block of air freshening material in which the casing has discharge slots through which, in use, vapour from the air freshening material is dispensed into the atmosphere. Such a container is mounted on any convenient surface adjacent the area in which air freshening vapour is required to be dispensed. During use, the block of material decreases in overall size as the material decomposes or evaporates, and in practice it is found that its effectiveness declines as the block becomes smaller.

In British Patent Application No. 2274781 there is described an air freshening system in which a container housing air freshening material has discharge apertures and is mounted on an intermittently movable member such as a door, whereby movement of the member causes a dose of air freshening material to be dispensed from the container through the discharge apertures. The air freshening material is formed of impregnated granules contained in a sachet which is permeable to the air freshening vapour and thus the air freshening material evaporates in the same manner as a block.

SUMMARY OF THE INVENTION

According to one aspect of the invention there is provided an air freshener unit comprising a container, a disc-shaped cartridge of air freshening material rotatably mounted within the container for rotation about a substantially horizontal axis, and a discharge outlet in the wall of the container allowing air freshening vapour to be dispensed, wherein the container has baffle means adapted to allow a faster rate of evaporation of the air freshening material in one part of the cartridge relative to the remainder of the cartridge, said one part being at least partially offset with respect to a vertical line through the axis of rotation, whereby the quicker rate of evaporation in the offset part will by itself cause the centre of gravity of the cartridge to change and thereby the cartridge to self-rotate within the container.

Preferably the offset part of the cartridge is additionally located at least partially and may be wholly below the axis of rotation of the cartridge.

It is also preferred that the container comprises an outer casing spaced forwardly from an inner enclosure within which the cartridge is rotatably mounted to form a compartment between the outer casing and the inner enclosure, the inner enclosure providing said baffle means and having at least one outlet through which the offset part of the air freshening material is directly open to said compartment, and the discharge outlet being in a wall of the outer casing forming the compartment.

The outer casing preferably has at least one vent which provides an air flow into the compartment between the outer casing and the inner enclosure and thereby allows for increased evaporation of the air freshening material in the offset part.

The back of the container preferably has means for attachment of the unit to a vertical surface.

In one embodiment, the unit is attached to an intermittently movable member, e.g. a door, whereby movement of the member causes a dose of air freshening vapour to be discharged through said outlet.

In an alternative embodiment, the unit includes a fan for causing a continuous or intermittent dose of air freshening vapour to be discharged through said outlet in the wall of the container.

The invention also provides a disc-shaped cartridge of air freshening material for an air freshener unit as defined above, wherein the cartridge comprises a holder having a hub portion for rotatably mounting the cartridge in the container, and holding means for supporting air freshening material in block form uniformly around the hub portion, the hub portion having oppositely directed stub shafts for location in apertures in opposed walls of the container between which the cartridge is to be mounted, the apertures allowing the cartridge to rotate. The apertures preferably provide bearing surfaces for the stub shafts.

In one embodiment the holding means provides at least one annular channel surrounding the hub portion of the holder which holds an annular block of air freshening material. The channel may have radial divisions forming individual pockets for holding separate segments of air freshening material.

In an alternative embodiment the holding means is an arrangement of spokes extending outwardly from the hub portion of the holder, which spokes are embedded in an annular block or separate segments of air freshening material. This embodiment of cartridge may be formed in an open mould, the holder being inserted into the mould before the air freshening material is introduced or before the material has set, and the mould being subsequently covered with a protective sheet or film which is peeled off before removal of the cartridge from the mould for loading into an air freshening unit.

The spokes may be interconnected by arcuate plates which are also embedded in the annular block or separate segments of air freshening material. The plates may be perforated allowing the air freshening material to pass therethrough.

If desired, the air freshening material may be formed of at least two different vapour discharging materials.

The invention provides an air freshener unit as defined above including a cartridge as defined above.

According to a further aspect of the invention there is provided a method of discharging different air freshening vapours from the same air freshener unit, the method comprising providing first and second vapour discharging materials disposed circumferentially displaced in a disc-shaped cartridge of air freshening material, and mounting the cartridge for rotation within a container having baffle means adapted initially to restrict the evaporation of the second material relative to the first material, the evaporation of said first material causing the centre of gravity of the cartridge to change and thereby the cartridge to self-rotate relative to the baffle means until the baffle means restricts the evaporation of the first material relative to the second material whereupon vapour from the second material is discharged.

DESCRIPTION OF THE PREFERRED EMBODIMENTS

Referring to FIGS. 1 to 5, there is shown an air freshening unit 10 for attachment to the surface of a door 11 or other intermittently movable member, for example the inside surface of a bathroom door. The unit comprises an outer casing 12 which is clipped by lugs 13 to an inner enclosure 14 within which a disc-shaped cartridge 15 of air freshening material 16 is rotatably mounted for rotation about a horizontal axis.

The back of the inner enclosure has vertical grooves 17 for strips of adhesive tape 18 which allow the unit to be attached to the door surface. The outer casing 12 can then be pulled off for insertion or replacement of the cartridge 15, if necessary.

The outer casing 12 is spaced forwardly in this embodiment from the inner enclosure 14 to form a compartment 19 therebetween having a discharge outlet 20 in the bottom side of the peripheral wall. Vents 21 in opposite sides of the outer casing allow air to enter the compartment from either side and internal spacer walls 22 inhibit air flow directly from the vents 21 to the discharge outlet 20.

The forward wall 23 of the inner enclosure 14 has an outlet 24 through which air freshening vapour can collect in the compartment 19 and then pass out of the unit through the discharge outlet 20. Some vapour may also pass out through the vents 21, but the primary purpose of the vents is to allow a temporary increased air flow into the compartment 19. Thereby, on movement of the door 11, a pulse of air flows into the compartment 19 which causes a concentrated dose of air freshening vapour which has previously collected in the compartment to be discharged from the unit.

The forward wall 23 of the inner enclosure 14 also provides a baffle which, by means of the outlet 24, exposes only a part 25 of the air freshening material of the cartridge 15 directly to the compartment 19 and thereby allows a faster rate of evaporation in part 25 relative to the evaporation of the remainder of the air freshening material. The outlet 24 and thereby the exposed part 25 is partially offset with respect to a vertical line through the axis of rotation. The quicker rate of evaporation in the offset part 25 will by itself cause the centre of gravity of the cartridge to change and thereby the cartridge to self-rotate within the inner enclosure 14. A different part or surface area of the air freshening material will then become exposed to the compartment and will evaporate at the faster rate. For achieving self-rotation of the cartridge 15, the outlet 24 through which the part 25 of the air freshening material is exposed to the compartment 19 is both at least partially offset with respect to a vertical line through the axis of rotation of the cartridge 15 and preferably at least partially below the axis of rotation. In this embodiment, the outlet 24 is located in the lower half of the wall 23 and biased towards the lower right quartile of the wall as viewed in FIG. 2.

Figure 1:
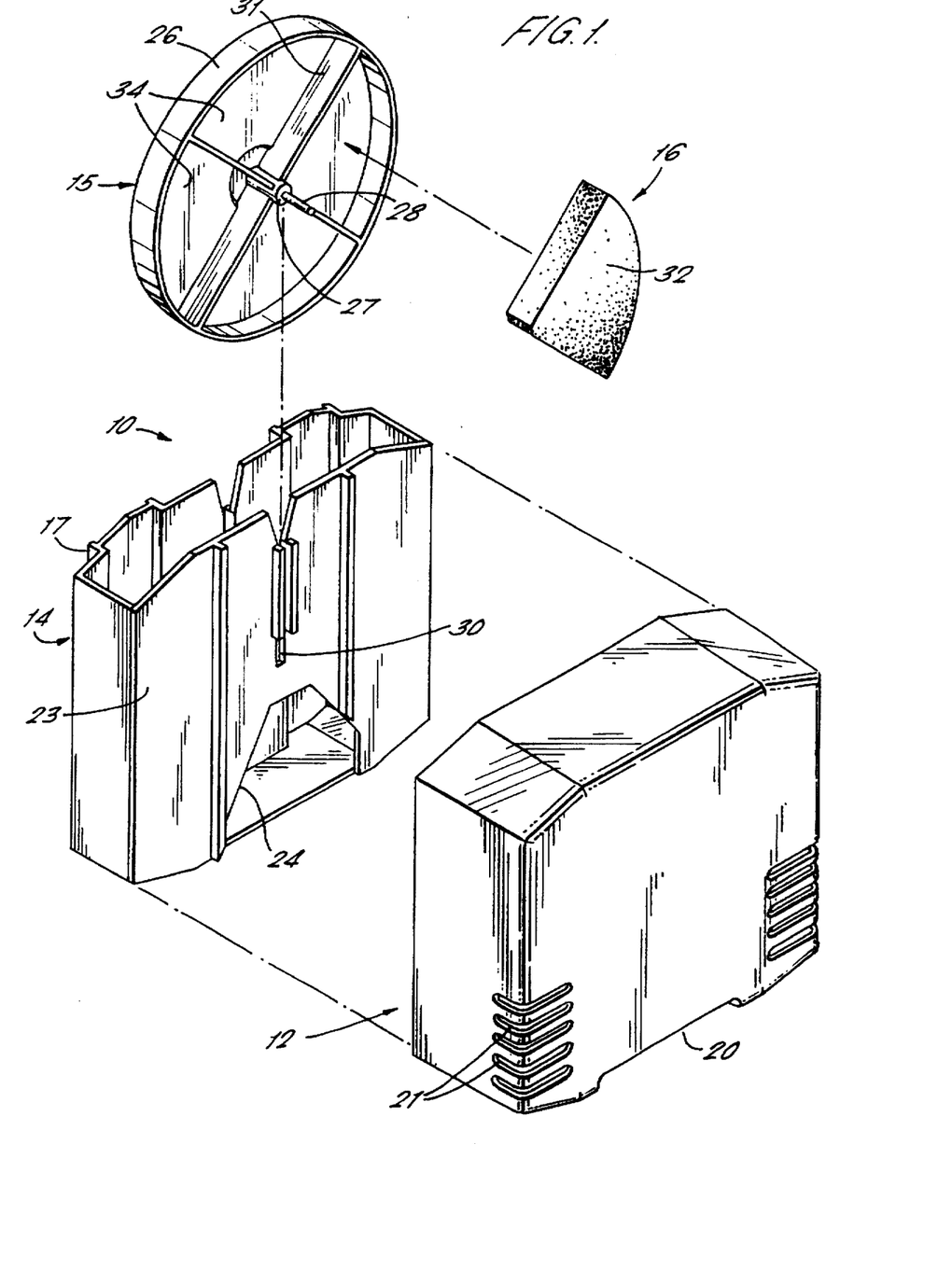
FIG. 1 is a perspective view, by way of example, of an air freshening unit, in exploded form.
Figure 2:
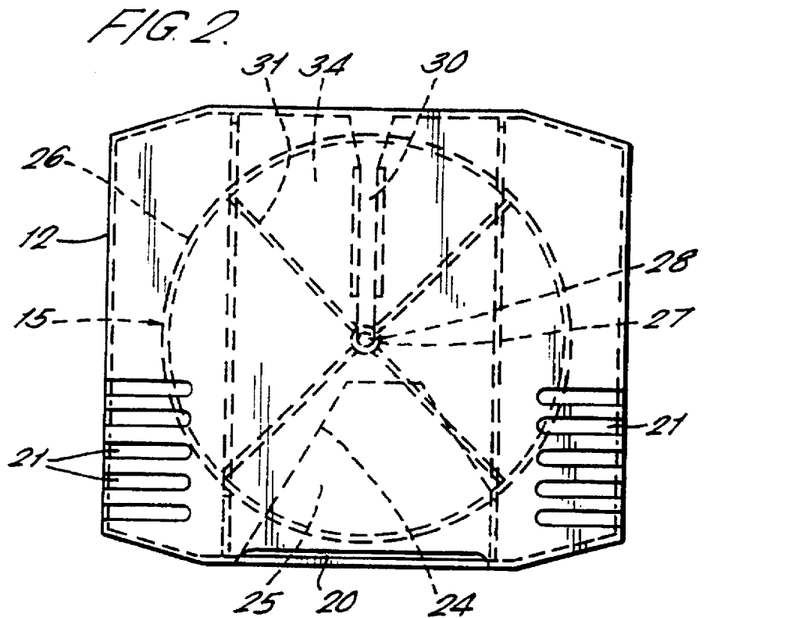
FIG. 2 is a front view of the assembled unit of FIG. 1.
Figure 3:
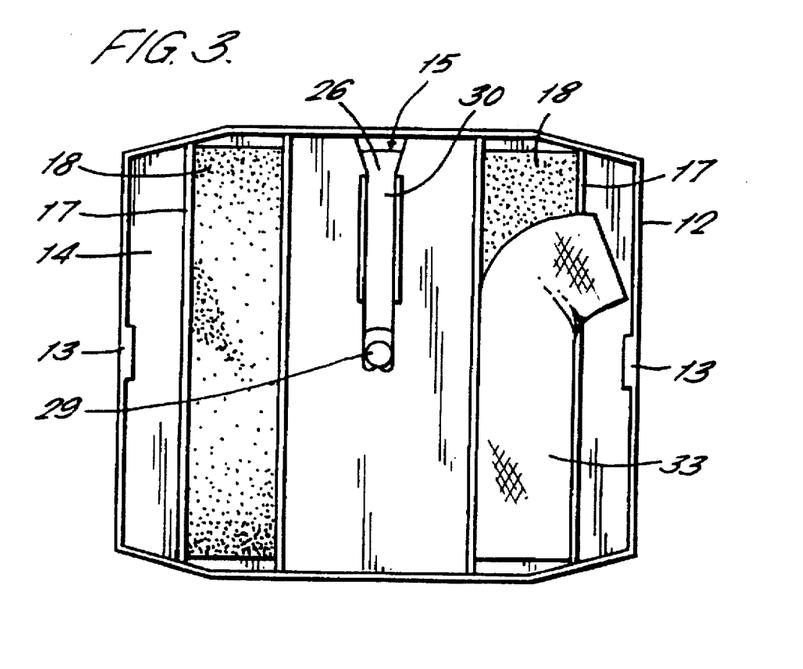
FIG. 3 is a rear view of the unit of FIG. 1.
Figure 4:
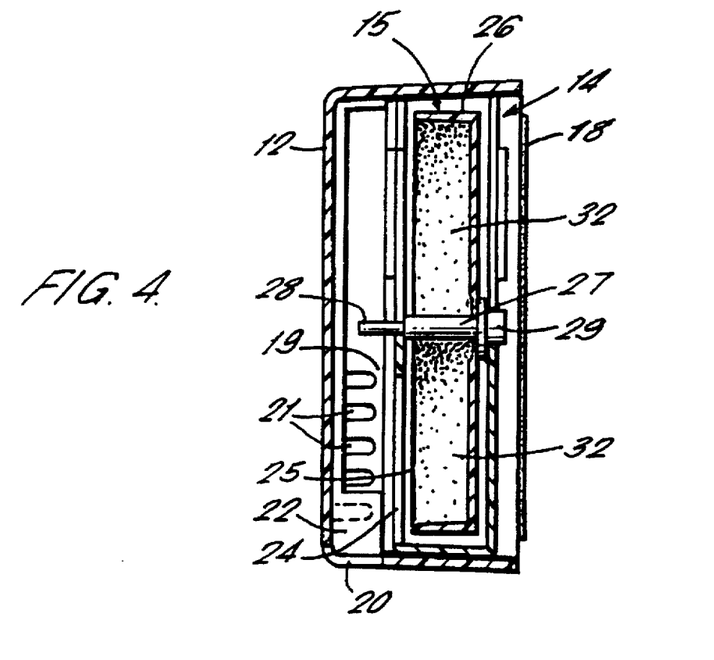
FIG. 4 is a vertical section of the unit of FIG. 1 through the axis of rotation of the cartridge showing the compartment between the outer casing and the inner enclosure.

The cartridge 15 is a holder 26 which supports the air freshening material and has a hub portion 27 provided with oppositely directed stub shafts 28,29 which engage respective vertical slots 30 in the forward and back walls of the inner enclosure 14, the slots being open at their upper ends. The walls at the lower ends of the slots 30, or alternatively apertures defined by the walls of the slots, provide bearing surfaces for the stub shafts 28,29 to allow the holder to freely rotate. In this embodiment, the holder 26 has one closed face and equally spaced divisions 31 extending radially from the hub portion 27, thereby forming four pockets for receiving separate blocks 32 of air freshening material which are circumferentially displaced one from the other uniformly around the hub portion. Each block 32 may be an air freshening gel in solid form or may comprise a substrate impregnated with an air freshening vapour. In either case the air freshening material evaporates to give off a vapour when it is exposed to air. In this embodiment two of the blocks 32 are of a different material, i.e. they give off a different vapour, from the other two blocks, and the different materials are disposed alternately within the pockets of the holder. The slots 30 are of different widths to correspond with the respective stub shaft of the holder so that the cartridge can only be loaded with the open face adjacent the forward wall 23 of the inner enclosure 14. The holder is conveniently moulded of plastics material and is relatively lightweight whereby it does not prevent evaporation of the air freshening material in the exposed part 25 from causing the cartridge as a whole to self-rotate within the inner enclosure.

Figure 5:
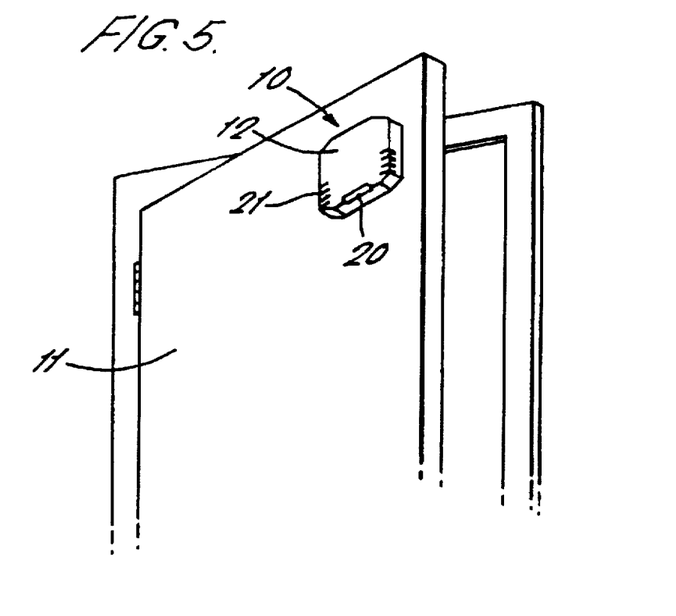
FIG. 5 shows the unit of FIG. 1 attached to the surface of a door.

In use, the unit 10 is pre-loaded with a cartridge 15 of air freshening material or is loaded with a cartridge 15 after removing any wrapping material and inserting the stub shafts 28,29 of the holder into the slots 30 of the inner enclosure 14 with the open face of the air freshening material adjacent the forward wall 23 of the inner enclosure. Part 25 of the air freshening material will then be exposed by the offset outlet 24 in the wall 23. The outer casing 12 is clipped onto the inner enclosure 14 with the discharge outlet 20 lowermost. Masking paper 33 is removed from the adhesive tape 18 on the back of the inner enclosure, and the unit is attached to the inner surface of a door 11 as shown in FIG. 5.

The exposed part 25 of the air freshening material will evaporate more than the remainder of the material, and air freshening vapour from that part 25 will collect in the compartment 19 and some discharge will occur. However, movement of the door will cause a pulse of air to flow into the compartment and a concentrated dose of vapour will be discharged into the atmosphere. The exposed part 25 will also be excited to evaporate further and to refill the compartment ahead of the next movement of the door. The uneven evaporation of the air freshening material as a whole and the fact that the part which is evaporating faster is offset vertically from the axis of rotation causes the centre of gravity of the cartridge to change and the cartridge to self-rotate. Thereby a different part 25 of the air freshening material becomes exposed to the outlet 24. It is also found that the remainder of the air freshening material which is restricted from evaporation by the baffle effect of the forward wall 23 of the inner enclosure 14, regenerates itself so that when it next becomes exposed, it evaporates faster than would otherwise be the case if it was continuously exposed. By providing different air freshening materials circumferentially displaced as described above, the different vapours or flavours are evaporated successively as the cartridge rotates.

Figures 6, 7:
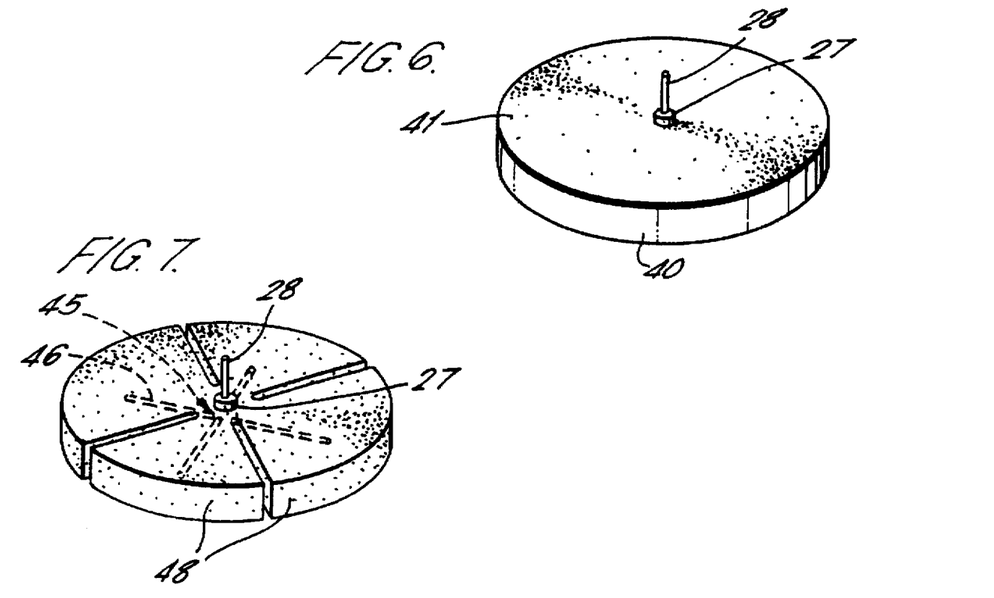
FIG. 6 shows another cartridge for use in the unit of FIG. 1.
FIG. 7 shows a further cartridge for use in the unit of FIG. 1.

FIG. 6 shows an alternative cartridge in which the holder 40 is formed without radial divisions and receives an annular block 41 of air freshening material. Such a block would normally be formed of one type of vapour discharging material.

In FIG. 7 there is shown a further form of cartridge in which holder 45 has a spoked arrangement in which four spokes 46 extend radially from the hub portion 27. The spokes 46 are embedded in circumferentially spaced segments 48 of a block of air freshening material, and as each segment evaporates it will give off the desired vapour. If desired, materials which give off different vapours may be incorporated in a single cartridge in the same manner as in the embodiment of FIGS. 1 to 5.

Figure 8:
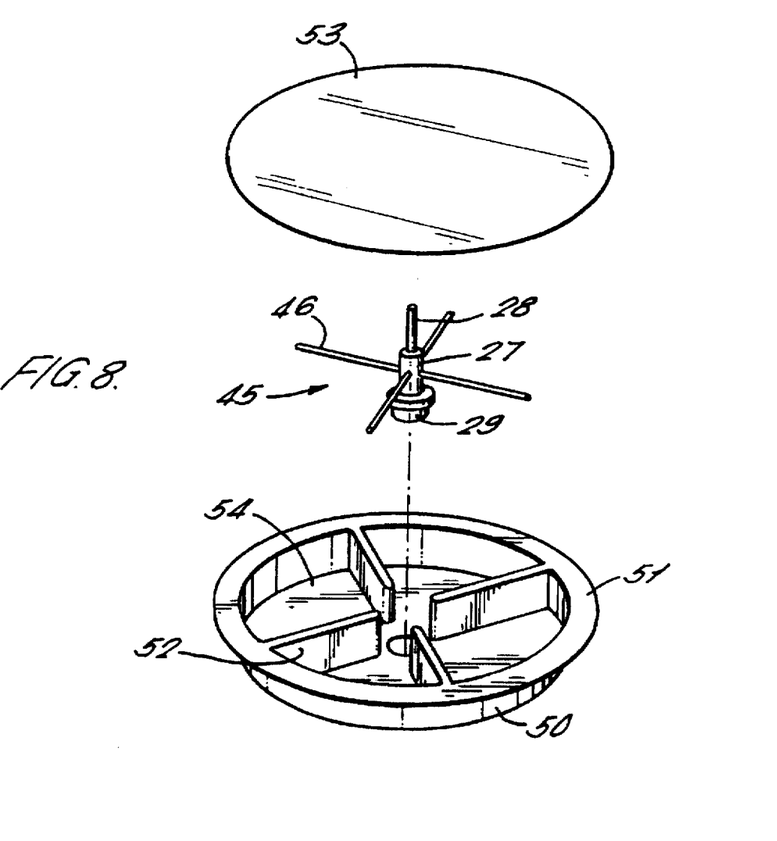
FIG. 8 illustrates a mould for forming the cartridge of FIG. 7.

FIG. 8 relates to a method of forming the cartridge of FIG. 7. There is provided a thin, vacuum-formed base mould 50 having a peripheral rim 51 and four radially extending divisions 52 which do not meet at the centre, but which generally define four pockets 54 within the mould. A holder 45 of the form shown in FIG. 7 is inserted into the mould 50 with the spokes 46 in respective pockets 54 and the hub 27 in the centre of the mould, either before the mould is filled with the desired air freshening material or materials, i.e. there may be different materials introduced into adjacent pockets, or prior to the material or materials becoming set. Subsequently the top surface of the mould is covered by a suitable protective sheet or film 53 which is welded to the upper surface of the rim 51. In use, the protective film is peeled off and the cartridge removed from the mould. The cartridge can then be loaded into the air freshening unit of FIGS. 1 to 5.

A similar mould may be employed which does not have the divisions 52, whereby a cartridge is formed having the spokes 46 embedded in an annular block of air freshening material.

Figure 9:
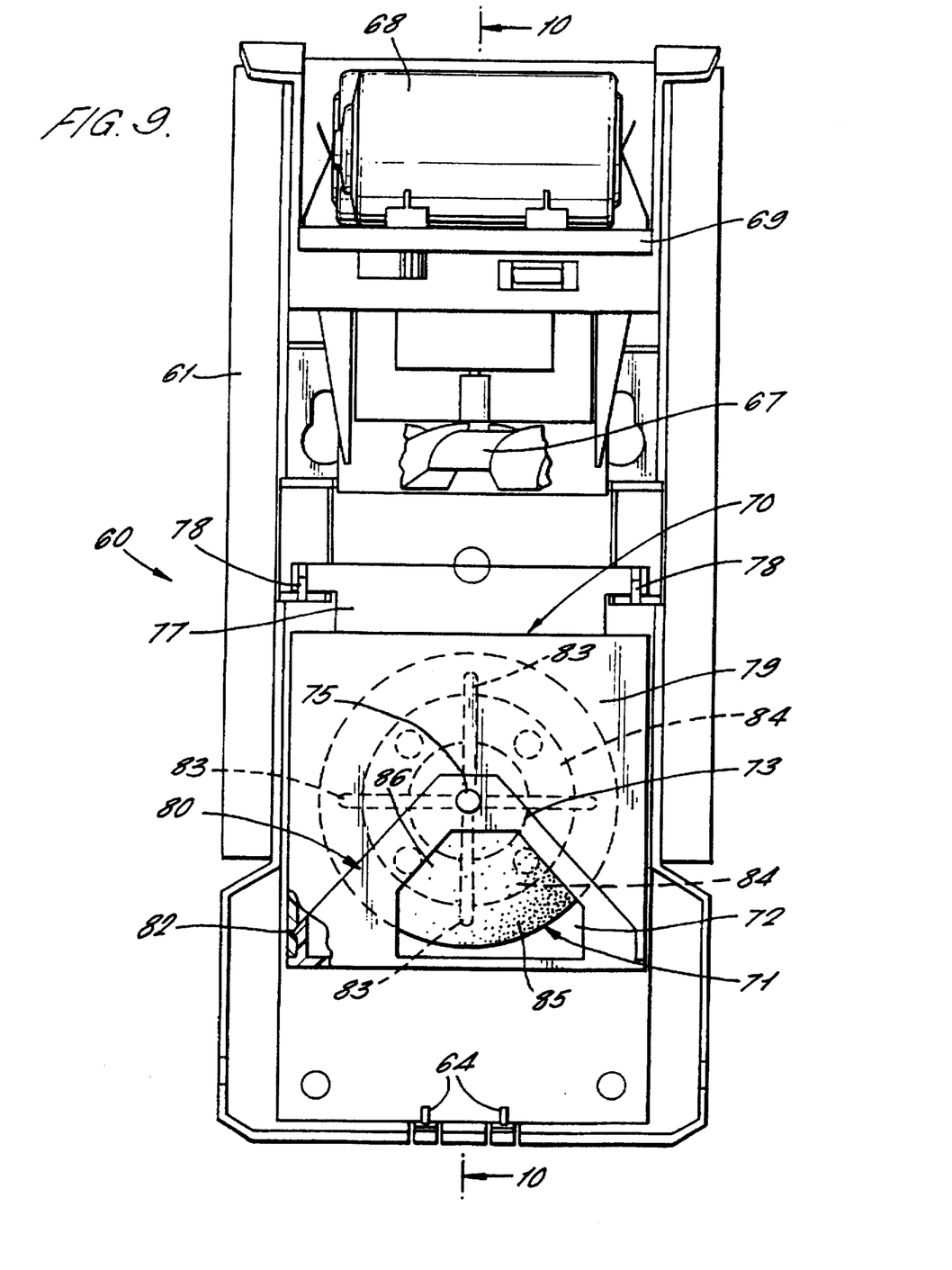
FIG. 9 is a front elevation, partly cut-away, of another embodiment of an air freshening unit, with the cover, front panel and an external baffle removed for clarity.
Figure 10:
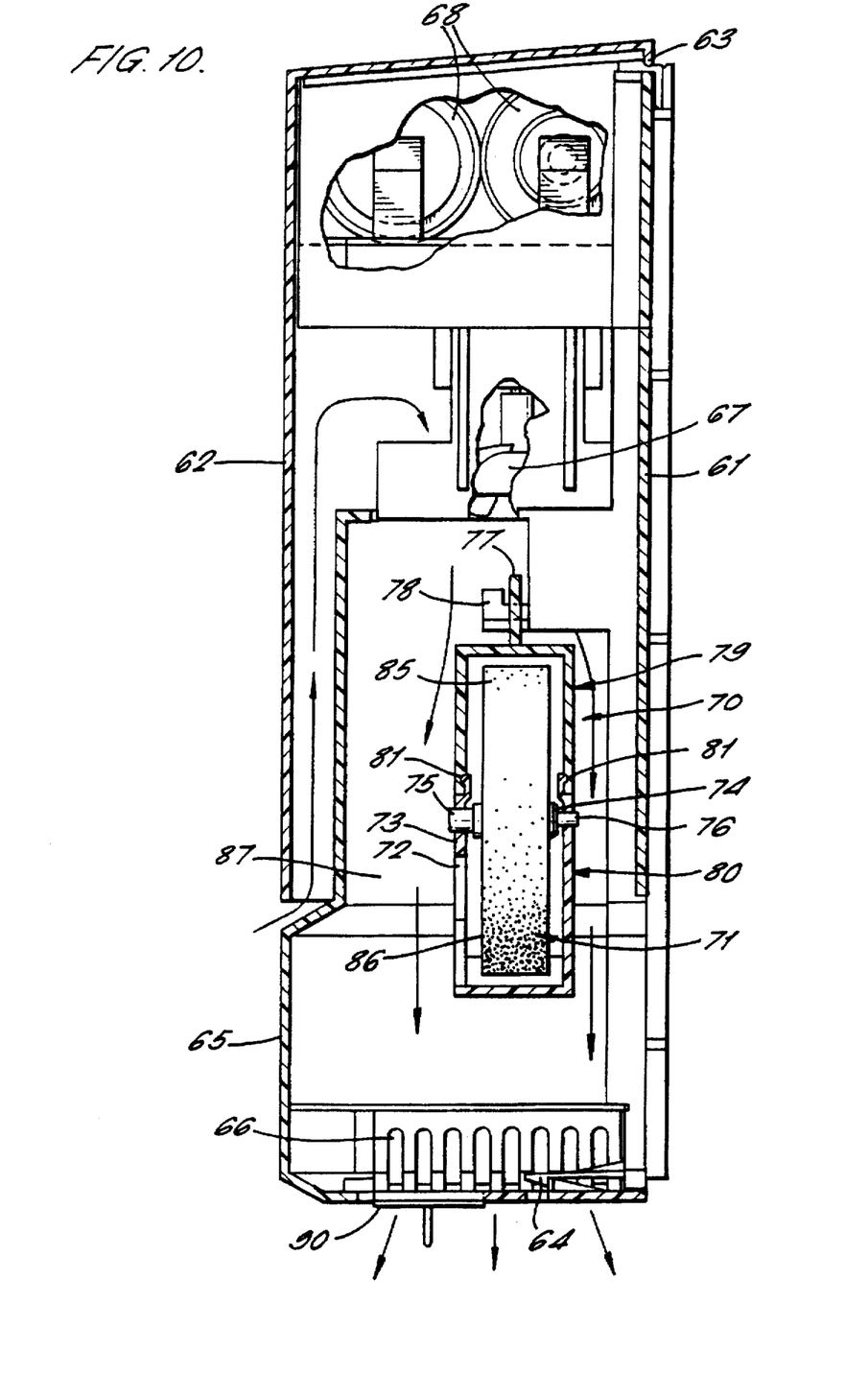
FIG. 10 is a section along line 10—10 in FIG. 9 of the complete unit.

With reference to FIGS. 9 and 10, there is shown a wall-mounted air freshening unit 60 having an enlarged outer casing relative to the previously described embodiments to provide a combined housing for the inner enclosure and cartridge and an electrically operated fan. The outer casing in this embodiment has a back plate 61 with apertures or other conventional means for attachment to a wall surface. Also, as shown in FIG. 10, a front cover 62 has a downwardly turned lip 63 or pair of lugs for removably clipping the cover to the top end of the back plate 61. Clipped to the bottom end of the back plate 61 by clips 64 is a front panel 65 which internally overlaps the cover 62 in spaced relation to create an entry air flow path between the panel and the cover. In the lower wall and partly in each side wall of the front panel 65 are slots 66 which provide one or more outlets or vents for vapour or fragrance. In this embodiment, an external baffle 90 (shown in FIG. 10 only) can be slid forwardly or rearwardly to adjust the open area of the outlet slots 66.

Supported on the back plate 61 in the upper zone of the unit is a conventional electric fan 67 which in this embodiment is operated by batteries 68 carried on a battery tray 69. Alternatively, the fan may be mains operated either continuously, or intermittently and controlled by suitable timing means.

Generally in the lower zone of the unit beneath the fan 67, there is suspended the inner enclosure 70 and rotatable cartridge 71. The inner enclosure 70 is, in principle, similar to the inner enclosure 14 of the embodiment of FIG. 1, and likewise has an outlet 72 in the lower half of the front wall 73 of the inner enclosure and biased towards the lower right quartile of the front wall as viewed in FIG. 10 so that it is offset relative to a vertical line through the axis of rotation of the cartridge 71. For rotatably mounting the cartridge within the enclosure 70, the cartridge has a hub portion 74 and stub shafts 75,76. Also, in this embodiment, as in the case of the previous embodiment of FIG. 7, the stub shafts are of different diameters which means that the cartridge cannot be reversed in the enclosure 70.

The inner enclosure 70 has a T-shaped bar 77 which extends upwardly for suspending the enclosure on a pair of hooks 78 protruding forwardly from the back plate 61. The cartridge can thereby freely self-rotate within the enclosure 70 as evaporation takes place. In this embodiment, the cartridge 71 is inserted into the enclosure from below rather than above. This is achieved by forming the inner enclosure 70 of an upper holder part 79 and a lower A-frame 80 on which the cartridge 71 is rotatably supported and which provides the outlet 72 in the front wall 73. The stub shafts 75,76 are snapped into apertures in the A-frame 80, which provide bearing surfaces therefor, and the A-frame is itself snapped into holder part 79 by a pair of lugs 81 at its apex (FIG. 10) and a pair of lugs 82 on one end of its base (one of which lugs 82 is shown in FIG. 9).

For supporting the annular block 85 of air freshening material around the hub portion 74, there are provided four spokes 83, in a similar manner to the embodiment of FIG. 7, which, in this embodiment, are interconnected circumferentially of the cartridge by arcuate plates 84, each plate which interconnects two adjacent spokes having at least one perforation allowing the material of the block to pass therethrough.

The cartridge 71 is moulded in a similar manner to the cartridge of FIGS. 7 and 8 whereby the spokes 83 and the arcuate plates 84 become embedded as holding means in the air freshening material. Again, as in the cartridge of FIG. 7, materials which give off different vapours may be incorporated in circumferentially spaced relation in the block 85.

In use, the desired cartridge 71 is snapped into the inner enclosure 70 which is hung on the hooks 78 with the outlet 72 facing forwardly of the unit. The front panel 65 and the cover 62 are then separately clipped onto the back plate. Evaporation of the air freshening material of the block 85 occurs as described previously. The part 86 exposed by the outlet 72 will evaporate more than the remainder of the material, and air freshening vapour or fragrance from the exposed part will collect in compartment 87 within the lower half of the unit. Operation of the fan 67 will draw an inflow of air upwardly into the unit through the gap between the cover 62 and the front panel 65 and then downwardly past the inner enclosure 70 thereby transporting the evaporated vapour or fragrance in compartment 87 out of the unit through those slots 66 which are not shut off by the baffle 90. The exposed part 86 of the air freshening material of the cartridge 71 will be excited to evaporate further and to provide a continuous discharge of vapour or fragrance from the inner enclosure 70 into compartment 87, which will be conveyed out of the unit with the assistance of the fan 67.

The uneven evaporation of the air freshening material as a whole and the fact that the outlet 72 is offset vertically from the axis of rotation of the cartridge 71 causes the centre of gravity of the cartridge to alter and the cartridge to self-rotate. Thereby a different part of the air freshening material becomes exposed to the outlet 72. If the cartridge is formed of different air freshening materials, the different vapours or flavours are evaporated successively as the cartridge rotates.

The invention is not restricted to the specific details of the embodiments described above. For example, in both the embodiments of FIGS. 1 to 5 and FIG. 7, the cartridge may have a different number of blocks of air freshening material, i.e. 2,3 or more than 4, each being of the same material or a plurality of different materials.

Also, the air freshening unit may be formed with the compartment 19 to the rear or to one side of the inner enclosure 14 instead of in front of the inner enclosure. In either case, the discharge outlet 20 and the vents 21 in the outer casing 12, and the outlet 24 in the inner enclosure 14 would be repositioned accordingly to allow for uneven evaporation of the air freshening material and the consequent self-rotation of the cartridge.

Furthermore, the unit may be readily adapted so that it is free-standing instead of being attached to a surface, the discharge outlet 20 being repositioned if necessary.

In any of the embodiments of FIGS. 1 to 8, instead of the air freshening unit being free-standing or mounted on an intermittently movable member, the unit may be wall mounted. In this case, as in the embodiment of FIGS. 9 and 10, the unit may include a fan for creating an air flow within the compartment 19 and thereby causing a continuous or intermittent increased dose of air freshening vapour to be dispensed through the discharge outlet 20 of the unit. The fan may be either battery or mains operated.

If desired, the air freshener unit may comprise a container equivalent of the inner enclosure 14 or 70 alone, i.e. without the outer casing, within which a cartridge 15 or 71 is rotatably mounted. In this case, the front wall of the container still provides the baffle which causes the air freshening material to evaporate unevenly and thus the cartridge to self-rotate, but the outlet 24 or 72 in the front wall becomes the discharge outlet of the unit.

What I claim is:

1. An air freshener unit comprising;
    a container,
    a disc-shaped cartridge of air freshening material rotatably mounted within the container for rotation about a substantially horizontal axis,
    a discharge outlet in the wall of the container for allowing air freshening vapour to be dispensed,
    said container comprising baffle means adapted to allow a faster rate of evaporation of the air freshening material in one part of the cartridge relative to the remainder of the cartridge, said one part of the cartridge being at least partially offset with respect to a vertical line through the axis of rotation, whereby the quicker rate of evaporation in the offset part will by itself cause the center of gravity of the cartridge to change and thereby cause the cartridge to self-rotate within the container, and
    wherein said cartridge comprises a holder having a hub portion for rotatably mounting the cartridge in the container, and holding means for supporting the air freshening material in block form uniformly around the hub portion, the hub portion having oppositely directed stub shafts for location in apertures in opposed walls of the container between which the cartridge is to be mounted, the apertures allowing the cartridge to rotate.

2. The air freshener unit according to claim 1, wherein the offset part of the cartridge is additionally located at least partially below the axis of rotation of the cartridge.

3. The air freshener unit according to claim 1, wherein the back of the container has means for attachment of the unit to a vertical surface.

4. The air freshener unit according to claim 1, wherein the back of the container has means for attachment of the unit to an intermittently movable member whereby, in use, movement of the member causes a dose of air freshening vapour to be discharged through said outlet in the wall of the container.

5. The air freshener unit according to claim 1, including a fan for causing a continuous or intermittent increased dose of air freshening vapour to be discharged through said outlet in the wall of the container.

6. The air freshener unit according to claim 1, wherein the apertures provide bearing surfaces for the stub shafts.

7. The air freshening unit according to claim 1, wherein the air freshening material is formed of at least two different vapour discharging materials.

8. The air freshener unit according to claim 1, wherein the container comprises an outer casing spaced forwardly from an inner enclosure within which the cartridge is rotatably mounted to form a compartment between the outer casing and the inner enclosure, the inner enclosure providing said baffle means and having at least one outlet through which the offset part of the air freshener material is directly open to said compartment, and the casing forming the compartment.

9. The air freshener unit according to claim 8, wherein the outer casing has at least one vent which provides air flow into the compartment between the outer casing and the inner enclosure and thereby allows for increased evaporation of the air freshener material in the offset part.

10. The air freshener unit according to claim 9, including a fan mounted in the air flow within the compartment between the outer casing and the inner enclosure.

11. The air freshener unit according to claim 1, wherein the holding means provides at least one annular channel surrounding the hub portion of the holder which holds an annular block of air freshening material.

12. The air freshener unit according to claim 11, wherein the channel has radial divisions forming individual pockets for holding separate segments of air freshening material.

13. The air freshener unit according to claim 1, wherein the holding means is an arrangement of spokes extending outwardly from the hub portion of the holder, which spokes are embedded in an annular block or separate segments of air freshening material.

14. The air freshener unit according to claim 13, wherein the cartridge is formed in an open mould, the holder being inserted into the mould before the air freshening material is introduced or before the material has set, and the mould being subsequently covered with a protective sheet or film which is peeled off before removal of the cartridge from the mould for loading into an air freshener unit.

15. The air freshener unit according to claim 13, wherein the spokes are interconnected by arcuate plates which are also embedded in the annular block or separate segments of air freshening material.

16. A method of discharging different air freshening vapours from the same air freshener unit, the method comprising providing first and second vapour discharging materials disposed circumferentially displaced in a disc-shaped cartridge of air freshening material, and mounting the cartridge for rotation within a container having baffle means adapted initially to restrict the evaporation of the second material relative to the first material, the evaporation of said first material causing the centre of gravity of the cartridge to change and thereby the cartridge to self-rotate relative to the baffle means until the baffle means restricts the evaporation of the first material relative to the second material whereupon vapour from the second material is discharged.

* * * * *